(12) United States Patent
Owen et al.

(10) Patent No.: US 9,617,466 B2
(45) Date of Patent: *Apr. 11, 2017

(54) STABILIZING ADDITIVES FOR THERMOCHROMIC PIGMENTS

(71) Applicant: Chromatic Technologies, Inc., Colorado Springs, CO (US)

(72) Inventors: Timothy J. Owen, Colorado Springs, CO (US); Terrill Scott Clayton, Colorado Springs, CO (US); Bryan M. Siske, Colorado Springs, CO (US); Christopher W. Roberts, Colorado Springs, CO (US); Vladimir Tomovich, Colorado Springs, CO (US)

(73) Assignee: Chromatic Technologies, Inc., Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,577

(22) Filed: Dec. 18, 2015

(65) Prior Publication Data

US 2016/0108309 A1  Apr. 21, 2016

Related U.S. Application Data

(63) Continuation of application No. 14/140,756, filed on Dec. 26, 2013, now Pat. No. 9,216,397.

(60) Provisional application No. 61/747,004, filed on Dec. 28, 2012.

(51) Int. Cl.

| | |
|---|---|
| C08K 9/00 | (2006.01) |
| C09K 9/00 | (2006.01) |
| B01J 13/20 | (2006.01) |
| B01J 13/18 | (2006.01) |
| C09D 5/26 | (2006.01) |
| A61K 8/11 | (2006.01) |
| C09D 11/50 | (2014.01) |
| C09B 67/08 | (2006.01) |
| C09B 67/02 | (2006.01) |
| A61K 8/36 | (2006.01) |
| A61Q 1/02 | (2006.01) |
| B41M 5/28 | (2006.01) |

(52) U.S. Cl.
CPC ............. *C09K 9/00* (2013.01); *A61K 8/11* (2013.01); *A61K 8/361* (2013.01); *A61Q 1/02* (2013.01); *B01J 13/18* (2013.01); *B01J 13/20* (2013.01); *C09B 67/0013* (2013.01); *C09B 67/0097* (2013.01); *C09D 5/26* (2013.01); *C09D 11/50* (2013.01); *A61K 2800/412* (2013.01); *A61K 2800/438* (2013.01); *B41M 5/287* (2013.01)

(58) Field of Classification Search
CPC .............. C09D 5/26; B01J 13/20; B01J 13/18
See application file for complete search history.

(56) References Cited

U.S. PATENT DOCUMENTS

| | | | |
|---|---|---|---|
| 4,028,118 | A | 6/1977 | Nakasuji |
| 4,442,429 | A | 4/1984 | Kotani et al. |
| 4,902,604 | A | 2/1990 | Yamaguchi et al. |
| 5,350,633 | A | 9/1994 | Sumii et al. |
| 5,503,781 | A | 4/1996 | Sumii et al. |
| 5,558,700 | A | 9/1996 | Shibahashi et al. |
| 5,591,255 | A | 1/1997 | Small et al. |
| 5,785,746 | A | 7/1998 | Kito et al. |
| 6,139,779 | A | 10/2000 | Small et al. |
| 6,458,872 | B1 * | 10/2002 | Ravichandran ...... C07D 249/20 524/89 |
| 7,332,109 | B2 | 2/2008 | Senga et al. |
| 8,883,049 | B2 | 11/2014 | Clayton et al. |
| 9,216,397 | B2 * | 12/2015 | Owen ...................... B01J 13/20 |
| 2002/0132725 | A1 | 9/2002 | Labarge et al. |
| 2012/0148644 | A1 | 6/2012 | Popplewell |
| 2015/0076423 | A1 | 3/2015 | Clayton et al. |

FOREIGN PATENT DOCUMENTS

JP  2002102680  4/2002

OTHER PUBLICATIONS

U.S. Appl. No. 61/747,004, filed Dec. 28, 2012.
U.S. Appl. No. 14/140,756, filed Dec. 26, 2013.
PCT International Patent Application No. PCT/US2013/077849; International Search Report and Written Opinion mailed Oct. 31, 2014, 13 pages.

* cited by examiner

*Primary Examiner* — Hannah Pak
(74) *Attorney, Agent, or Firm* — Craig R. Miles; CR Miles P.C.

(57) ABSTRACT

A microencapsulation process is improved by adding a stabilizing agent that contains one or more catalytic organometal oxide materials, such as metal soaps. This functions as a crosslinker by causing unsaturated bonds in the microcapsule walls to react, thereby stabilizing the microcapsules against the effects of additives to coatings that, otherwise, degrade the functionality of thermochromic or photochromic materials at the microcapsule core.

20 Claims, No Drawings

STABILIZING ADDITIVES FOR THERMOCHROMIC PIGMENTS

This United States Patent Application is a continuation of U.S. patent application Ser. No. 14/140,756, filed Dec. 26, 2013, now U.S. Pat. No. 9,216,397, issued Dec. 22, 2015, which claims the benefit of U.S. Provisional Patent Application No. 61/747,004, filed Dec. 28, 2012, each hereby incorporated by reference herein.

BACKGROUND

Thermochromic materials undergo color changes in response to thermal exposure. This is frequently discussed in context of a hysteresis plot where color is activated and deactivated by thermal cycling. This hysteresis is shown, for example, in U.S. Pat. No. 4,442,429 issued to Kotani et al. The materials may be designed for specific applications to have little thermal separation between the different sides of the plot, or a large separation. Other aspects of performance design may include the thermal activation temperature.

Thermochromic pigments are conventionally made by well-known manufacturing processes. Typically, a leuco dye, a developer, oil, and a polymer, such as melamine formaldehyde or urea formaldehyde, are combined and agitated to create a very fine emulsion. The properties of the emulsion are such that the oil dye, and developer reside within a polymer formaldeyde capsule. Melamine formaldehyde is a thermo set resin similar to formica. The substance is very hard and will not break down at high temperature. This material is almost entirely insoluble in most solvents, but it is permeable. Thus, U.S. Pat. No. 5,591,255 issued to Small et al. advances the art by advising to forego use of additives that may permeate the capsules, especially certain ketones, diols, aldehydes, amines and aromatic compounds.

Even so, emerging new applications for thermochromic pigments demand the use of additives that interfere with functionality of the thermochromic pigments. By way of example, uses are emerging for thermochromic pigments that may be mixed with epoxy or polyester vehicles to form metal deco coatings. If desired, as suggested by U.S. Pat. No. 4,425,161 issued to Shibahashi et al., the thermochromic pigments may be used in combination with such polymers as, hydrocarbon resin, acryl resin, vinyl acetate resin, halogen-containing resin, diene resin, polyester resin, polyamide resin, polyurethane resin, epoxy resin, melamine resin and polyurea resin. This may necessitate the addition of auxiliary solvents including such diluents as high boiling point aromatic hydrocarbon solvents, waxes, terpene oils and fluorocarbon oils, as well as solvents to improve the rheology of the coatings. Thermochromic pigments blended with these materials have typically a short shelf life. Moreover, the materials in these vehicles may significantly alter the thermochromic behavior of the pigments, such as by suppressing the color activation temperature or varying the width of the hysteresis window.

Known processes for microencapsulation of thermochromic or photochromic materials include, for example, those disclosed in U.S. Pat. No. 4,028,118 issued to Nakasuji, U.S. Pat. No. 4,425,161 issued to Kito et al., U.S. Pat. No. 4,425,161 issued to Shibahashi et al., U.S. Pat. No. 4,902,604 issued to Yamaguchi et al., U.S. Pat. No. 5,350,633 issued to Sumii et al., U.S. Pat. No. 5,503,781 issued to Sumii et al., U.S. Pat. No. 6,139,779 issued to Small et al., and U.S. Pat. No. 7,732,109 issued to Senga et al., al. of which are incorporated by reference to the same extent as though fully disclosed herein.

SUMMARY

The presently disclosed instrumentalities advance the art and overcome the problems outlined above by providing improved thermochromic pigments that are stabilized against the deleterious effects of chemical additives that heretofore have damaged the pigments.

In one aspect, a stabilizing agent is combined with a slurry that contains thermochromic after the microcapsules are formed and cured. By way of example, this mixing may be done as the slurry is being mixed with a resin that is to be applied as an external coating on metal, such as an epoxy resin that may be applied to coiled aluminum stock for making beverage cans. Other useful resins include polyester resins, styrene resins, acrylates, and any other synthetic resins.

The stabilizing agent may be a metallocene catalyst or transition metal bonded to organic moieties through oxygen linkages. Preferred forms of the stabilizing agent are transition metal soaps, or any other carboxylic acid salt including a catalytic metal-oxygen moiety. The organic tail of these preferred materials improves solubility and dispersion. Zirconium 2-ethyl hexanoate is particularly preferred.

In one aspect, Formula (1) below shows the structure of a carboxylate salt that may be used as described herein:

$$M^n(R)n;$$

where M is a metal as described above of oxidation state n; and R is a carboxylate having a carbon number ranging from five to fourteen. M is preferably a transition metal. R is preferably a branched derivative of hexanoic acid, such as 2-ethyl hexanoate.

In another aspect, a metallocene catalyst may be provided with transitions metals bonded to oxygen, nitrogen, and/or halogen atoms.

It has been discovered that the materials described above have the surprising effect of protecting the color activation temperature of microcapsules in solvent based coatings. Without being bound by theory, it appears that these materials attack unsaturated multiple bonds, especially pi bonds, at the exterior surfaces of the microcapsules. In the absence of excess hydrogen, these bonds crosslink to make the microcapsules less permeable to deleterious additives that are, otherwise, capable of degrading the functionality of the materials forming the core of the microcapsules. In addition, the crosslinking effect protects the microcapsule without necessarily attacking unsaturated bonds at the surface of the microcapsules. Thus, the stabilizing agent may be combined with any form of commercially available microencapsulated thermochromic pigments to beneficially affect the performance of the pigments in any formulation for any intended environments of use. The microcapsules stabilized in this manner may be used in all applications for thermochromic pigments including, for example, thermochromic inks, paints, and coatings, in addition to cast or injected articles of manufacture. Moreover, this manner of stabilizing the microcapsules has additional uses in other microencapsulated materials, such as scented microcapsules, and photochromic microcapsules. The amount of stabilizing agent suitably ranges from 0.5% to 15% by weight of the slurry.

DETAILED DESCRIPTION

The following embodiments teach by way of example and not by limitation.

Example

Thermochromic microcapsules are incorporated into a solvent based high molecular weight epoxy coating where the solvent package contains polar solvents such as methyl isobutyl ketone, 2-butoxy ethanol, and n-butanol for example. The coating is then cured at a temperature above 200 C for a duration of 10 seconds to 30 seconds. In the absence of the stabilizing agent, the temperature profile of the thermochromic system is significantly repressed so that the full color development cannot be attained unless the coated sample is subjected to sub-zero temperatures for a period of time. By the addition of stabilizing additives such as a melamine resin (Cymel 303), metallic salts (zirconium ethyl hexanoate), and other agents which can accelerate crosslinking in the resin system surrounding the microcapsules, the microcapsule wall becomes more stable thus protecting the internal thermochromic properties. The effect is that the cured coating does not show a temperature repression for the full color development, even in the presence of the strongly polar solvents which are known to be harmful to the thermochromic properties of microcapsules. The effect of the stabilizing additive can be significant at concentrations of 0.5-15% by weight of the thermochromic coating.

We claim:

1. A slurry comprising:
   a photochromic or thermochromic material encapsulated within a microcapsule;
   a solvent-based vehicle; and
   a stabilizing agent comprising a metallocene catalyst or transition metal bonded to at least one organic moiety through an oxygen linkage, said stabilizing agent in an amount ranging from 0.5% to 15% by weight of said slurry;
   wherein said stabilizing agent is effective to stabilize said photochromic or thermochromic material encapsulated within said microcapsule against deleterious effects of said solvent-based vehicle.

2. The slurry of claim 1, wherein said transition metal comprises zirconium.

3. The slurry of claim 2, wherein said zirconium comprises zirconium 2-ethylhexanoate.

4. The slurry of claim 1, wherein said microcapsule is cured.

5. The slurry of claim 1, wherein said stabilizing agent protects a color activation temperature of said photochromic or thermochromic material encapsulated within said microcapsule in said solvent-based vehicle.

6. The slurry of claim 1, wherein a cured coating comprising said thermochromic material encapsulated within said microcapsule, said solvent-based vehicle, and said stabilizing agent does not show a temperature repression for full color development.

7. The slurry of claim 1, wherein said solvent-based vehicle comprises a polymer.

8. The slurry of claim 7, wherein said polymer is formulated for application as an external coating on metal.

9. The slurry of claim 8, wherein said metal comprises coiled aluminum stock.

10. The slurry of claim 8, wherein said metal is intended to form a beverage can.

11. The slurry of claim 1, wherein said solvent-based vehicle comprises at least one polar solvent.

12. A slurry comprising:
    a photochromic or thermochromic material encapsulated within a microcapsule;
    a solvent-based vehicle; and
    a stabilizing agent comprising a melamine resin, said stabilizing agent in an amount ranging from 0.5% to 15% by weight of said slurry;
    wherein said stabilizing agent is effective to stabilize said photochromic or thermochromic material encapsulated within said microcapsule against deleterious effects of said solvent-based vehicle.

13. The slurry of claim 12, wherein said microcapsule is cured.

14. The slurry of claim 12, wherein said stabilizing agent protects a color activation temperature of said photochromic or thermochromic material encapsulated within said microcapsule in said solvent-based vehicle.

15. The slurry of claim 12, wherein a cured coating comprising said thermochromic material encapsulated within said microcapsule, said solvent-based vehicle, and said stabilizing agent does not show a temperature repression for full color development.

16. The slurry of claim 12, wherein said solvent-based vehicle comprises a polymer.

17. The slurry of claim 16, wherein said polymer is formulated for application as an external coating on metal.

18. The slurry of claim 17, wherein said metal comprises coiled aluminum stock.

19. The slurry of claim 17, wherein said metal is intended to form a beverage can.

20. The slurry of claim 12, wherein said solvent-based vehicle comprises at least one polar solvent.

* * * * *